United States Patent [19]
Zdrok et al.

[11] 4,039,827
[45] Aug. 2, 1977

[54] METHOD FOR MARKING INTRAOCULAR LENSES

[75] Inventors: Edward Z. Zdrok, Webster, Mass.; Emil W. Deeg, Woodstock, Conn.

[73] Assignee: American Optical Corporation, Southbridge, Mass.

[21] Appl. No.: 717,819

[22] Filed: Aug. 26, 1976

[51] Int. Cl.² ............................................. G06K 7/10
[52] U.S. Cl. .................................. 250/271; 250/492 R
[58] Field of Search ................................ 250/271, 492

[56] References Cited

U.S. PATENT DOCUMENTS

| 2,937,279 | 5/1960 | Artandi et al. | 250/492 R |
| 3,556,794 | 1/1971 | Margerum | 250/492 R |
| 3,707,372 | 12/1972 | Hallman et al. | 250/492 A |

Primary Examiner—Harold A. Dixon
Attorney, Agent, or Firm—H. R. Berkenstock, Jr.; William C. Nealon

[57] ABSTRACT

Nondestructive marking of plastic artificial intraocular lenses for coding purposes. Exposure with ultraviolet radiation of portions of a lens surface forming boundaries of desired coding characters or similar exposure only of areas forming the characters themselves produces a differential in refractive index of the material of the lens wherewith detection and reading of the coding may be accomplished before and/or after intraocular implantation.

10 Claims, 9 Drawing Figures

METHOD FOR MARKING INTRAOCULAR LENSES

BACKGROUND OF THE INVENTION

1. Field of the Invention

Lens marking with particular reference to the coding of plastic artificial intraocular lenses (psuedophakoi) for establishing in each case of permanent record of particulars such as, for example, date and place of manufacture and monomer used.

2. Discussion of the Prior Art

In the manufacture, use, and sale of intraocularly implantable artificial lenses which are referred to in the art as psuedophakoi, it is essential for various reasons including law that a permanent record be made upon the article of particulars which may include date and place of manufacture and monomer used. Encoding with ciphers, i.e. seven characters and/or digits, affords countless separately identifiable bits of decodable information.

The application of such coding to the product, however, has heretofore presented serious problems for the following, to name a few, reasons:

The lenses of pseudophakoi are of necessity only approximately 5 mm in diameter and a center section of approximately 3 mm in diameter must be retained clear for visual use. Additionally, in each case, a substantial portion of the remaining approximately 1 mm margin must be utilized for attachment of the haptic section (lens clips) of the pseudophakos. Thus, there has been the serious problem of reducing character size of heretofore painted, leached, or engraved coding sufficiently to fit the space allowed while maintaining legibility. Additionally, painting, chemically leaching or engraving operations are not only difficult, tedious, time-consuming and expensive to perform particularly under the requirements of the aforesaid miniaturization of characters, but require special skills and equipment not always available or possible to make available at times and/or places of need.

Still further, painting, chemically leaching or engraving produce raised edges or depressions and systems of scratches or roughnesses which in any or all cases are potentially medically hazardous. Lens surface irregularities allow stagnation of body fluids and promote growth of micro-organisms. Surface interruptions or scratching caused by engraving can also be incipiative to lens material stressing or fissuring, either of which is potentially destructive to the lenses. Additionally, the inaesthetic readily discernable or undisguised nature of prior art coding by etching, leaching, or painting can be disconcerting to the observer of a pseudophakic and/or to the pseudophakic himself.

In view of the aforesaid and related drawbacks to prior art lens coding practices and with the urgent need for improvements in intraocular lens coding, it is an object of the present invention to provide a method for marking lenses which, in addition to being simple and economical to perform, will overcome the aforementioned and related problems and drawbacks of the prior art. More particularly, an object of the invention is to provide a method for marking lenses which, in addition to being simple and economical to perform, will provide readily decodable miniaturized caricatures undetectable to the naked eye, nondestructive to the lens article and nondisruptive of optimum surface smoothness but, on the other hand, readily discernable for interpretation either by direct reading or decoding with no more required than the aid of ordinary ophthalmological instruments.

Other objects and advantages of the invention will become more readily apparent from the following description.

SUMMARY OF THE INVENTION

The aforesaid and corollary objects of the invention are accomplished by exposing the ultraviolet radiation selected portions of a lens surface which either form the boundaries of desired coding characters or portions which are in the form of the coding characters themselves. This produces a differential in the refractive index of the lens material which renders detection and reading of the coding possible before and/or after intraocular implantation.

The coding process is nondestructive to material of the lens and noninterruptive to the smoothness of its customary optical finish. The method affords permanent recordation of pertinent lens data on the article itself in a medically safe manner and is aesthetically substantially invisible to the naked eye of an observer of a pseudophakic and nonobstructive to the pseudophakic's vision.

Details of the invention will become more readily apparent from the following description when taken in conjunction with the accompanying drawings in which.

Figure 3:
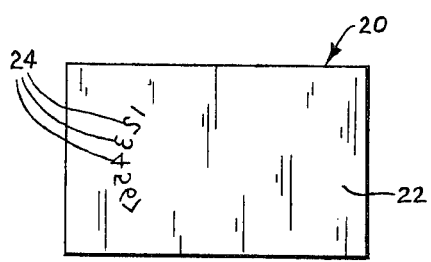
FIGS. 3 and 4 are plan views of masks which are useful in practice of the method of the invention.
Figure 4:
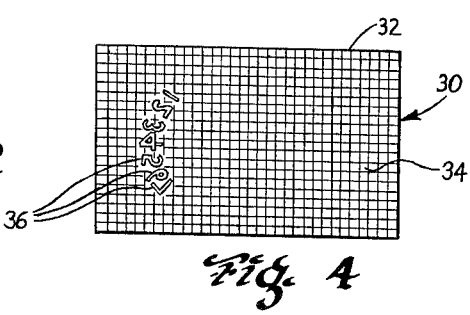
Figure 5:
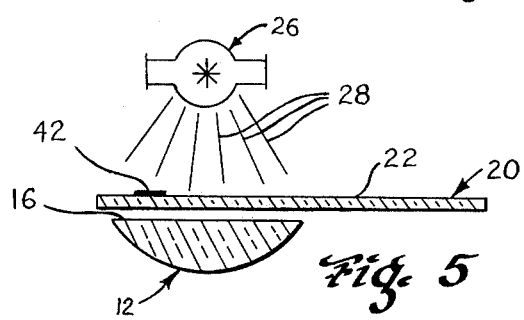
Figure 6:
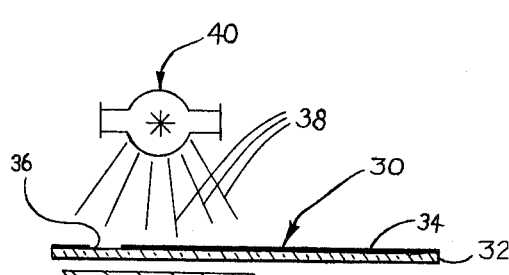
Figure 7:
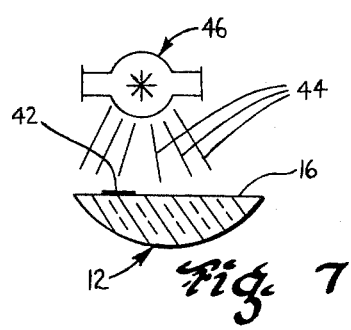
Figure 8:
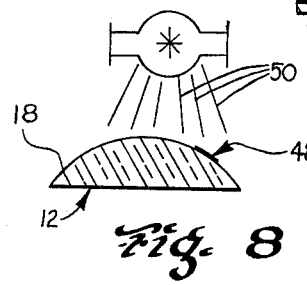
Figure 9:
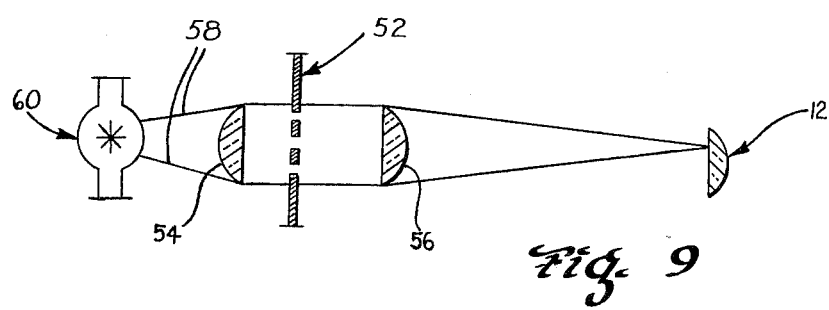

FIGS. 5 and 6 are diagrammatic illustrations of contemplated uses of the masks of FIGS. 3 and 4 respectively; and FIGS. 7, 8, and 9 are diagrammatic illustrations of modifications of the method of the invention.

DESCRIPTION OF THE PREFERRED EMBODIMENTS

Figure 1:
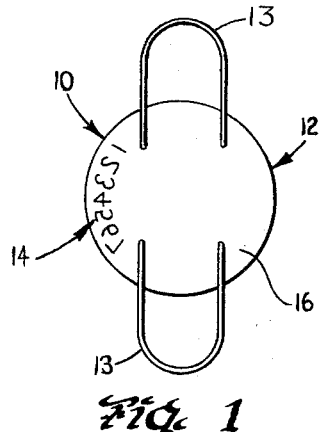
FIG. 1 is a view in rear elevation of an exemplary form of pseudophakos having coding applied thereto according to one technique contemplated by the invention.
Figure 2:
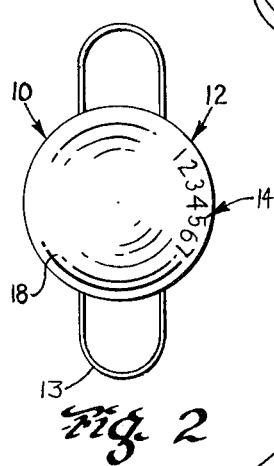
FIG. 2 is a front elevational view of the pseudophakos of FIG. 1.

In FIG. 1 and 2, there is illustrated one of the many forms of pseudophakoi currently used to produce retinal images and re-establishment of binocularity in cases of aphakia.

Pseudophakos 10 comprises an optical section (lens 12) and a haptic section (iris clips 13), the latter being in the form of posterior loops for iris diaphragm fixation.

While various forms of fixation devices including anterior and posterior loops, struts and/or clasps are used according to the needs and preferences of the surgeons, common to all is the lens whether plano-convex, double convex or of any other design. The plano-convex configuration of lens 12 has been selected here for purposes of illustrating principles of the invention. It should be understood, however, that the present method is applicable to any and all shapes and sizes of lenses.

Lens 12 is formed of a cast methylmethacrylate resin (e.g. biologically neutral, chemically pure polymethylmethacrylate) and its opposite sides are ground and optically polished.

The marking of lenses according to the invention involves the application thereto of a code 14 which may comprise letters, numbers, hieroglyphics or other symbols and/or combinations thereof. Numbers 1-7 have been used to illustrate the invention. For this illustration only, the code 14 has been shown in reverse image form on the posterior side 16 of lens 10 for reading in its true form from anterior side 18, i.e. the side facing the cornea after implantation.

The method of applying permanent markings such as code 14 according to the invention is as follows:

One surface of lens 12 is masked throughout areas thereof surrounding the code 14 or, alternatively, in areas forming the coding characters themselves. In connection with the latter, master 20 (FIGS. 3 and 5) which is in the form of a plate or slide 22 is constructed of a material such as quartz which is transparent to the short wavelengths of ultraviolet radiation. Painted, printed, transferred or otherwise applied to slide 22 are opaque masks 24 each in the configuration of a preselected code character. The masks 24 are arranged in a relative juxtaposition and preselected orientation corresponding to the arrangement desired of code 14.

With slide 22 interposed between lens 12 and a source 26 of ultraviolet radiation, preferably with the slide immediately adjacent to the posterior surface 16 of lens 12, the major portion of lens 12 is exposed to radiation 28 from source 6 while areas thereof corresponding in shape, size and position to masks 24 are shielded from such exposure.

This treatment alters the refractive index of the areas of lens 12 which are exposed to rays 28 leaving the areas protected by opaque masks 24 substantially unaltered in refractive index. The resulting refractive index differential produces a facsimilie of masks 24 which is readily discernable with the aid of side illumination and/or polarizing filters or variously reflected light.

Since the means which may be used to detect and read the facsimilie of masks 24 (i.e. the code 14) can be an ordinary slit lamp or any of many other forms and/or combinations of viewing aids including a simple magnifying glass, details of these instruments or devices will not be dealt with herein since they form no particular part of the present invention. The invention is related more particularly to matters of marking lenses by producing refractive index differentials in the form of coding in the lens bodies.

This refractive index differential need only be slight, e.g. in the order of 0.001 and while shown as being affected near the edge of lens 12, it may equally as well be applied to a more central portion of the lens if desired. Wherever placed, it will not adversely affect the pseudophakic's vision.

It should be understood that use of the expression "lens" in this specification and appendant claims is not intended to be exclusive of any or all of its various forms which may include buttons or blanks of lens stock whether unfinished or semifinished. Lens marking according to the invention may be effected before or after finishing of the lenses to their final shapes, sizes and/or surface textures.

Exemplary of reductions to practice of the invention are the following:

EXAMPLE I

Using a lens blank or button formed of polymethylmethacrylate of 12.7 mm diameter and 6.0 mm thickness having an index of refraction of 1.500, the unmasked portions thereof were exposed to ultraviolet radiation of approximately 2537 Angstroms at an intensity of approximately 940 microwatts/sq. cm. from a distance of approximately 5 cm. for a period of approximately 45 minutes. The result was the creation of a refractive index differential of approximately 0.001 penetrating at least 3mm of the blank or a change in refractive index of the exposed portion from 1.500 to 1.501 while the refractive index of portions of the lens protected by masks used to produce the code remained substantially unchanged, i.e. at 1.500.

EXAMPLE II

A similar result was obtained with a lens blank formed of polymethylmethacrylate but with a shorter exposure time of approximately 10 minutes at an intensity of 12,000 microwatts/sq. cm.; the distance between the lens and source of radiation was approximately 5 cm. and the wavelength of radiation was approximately 2537 Angstroms.

EXAMPLE III

A change in wavelength to 3660 Angstroms and intensity to approximately 160 microwatts/sq. cm. with other factors substantially similar to Examples I and II produced substantially the same results.

Ultra violet lamps used to effect the above-mentioned exemplary reductions to practice were obtained with Ultra-Violet Products, Inc. of San Gabriel, Calif. and are readily commercially available.

Referring more particularly to FIGS. 4 and 6, there is illustrated a technique for creating a change in refractive index of areas of lens 12 which are in the configuration of the code 14 characters themselves, i.e. the boundaries of these code characters and all remaining portions of the lens are shielded against the radiation used to produce the index differential in lens 12. Master 30 comprises slide 32 having opaque coating 34 extending over all portions thereof except areas 36 which are in the configuration of the code 14 characters to be applied to lens 12. Thus, ultraviolet radiation 38 from source 40 is permitted to impinge upon lens 12 substantially only in areas thereof immediately adjacent to the uncoated areas 36 of slide 32.

It should also be understood that masks such as 24 of FIGS. 3 and 5 or 34 of FIGS. 4 and 6 may be applied directly to the surface of the lens, if desired. For example, masks 42 similar to masks 24 of FIG. 3 may be applied to the posterior surface 16 of lens 12 and the lens accordingly exposed to ultraviolet radiation 44 from a suitable source 46 as shown in FIG. 7. Alternatively, similar masks 48 (FIG. 8) may be applied to the anterior surface of lens 12 and that surface of the lens exposed to ultraviolet radiation 50. It should be understood that while masks of the general type shown in FIG. 3 has been illustrated as in FIGS. 7 and 8, it is also contemplated that the form of masking illustrated in FIGS. 4 and 6 may be used directly upon either of the surfaces of lens 12 should the need or desire to do so arise.

For those interested in techniques available for producing masks such as those illustrated in FIGS. 3 and 4, there is a commercially available photographic image transfer system known to the trade as *i.n.t.* (image *n* transfer). It is sold by Industrial Graphics Division, 3M Company, St. Paul, Minnesota, USA. This has been found to offer a convenient, economical and highly effective system for producing masters 20 and 30 and/or code characters such as 42 and 48 (FIGS. 7 and 8) particularly in cases where a coding such as 14 need be of exceptionally small size yet readily legible. A photographic image transfer system permits the reduction of coding character size as desired with crisp, clear and readily discernable image reproduction. Image enlargement, of course, is possible whenever desired.

A modification of the method of the invention is illustrated in FIG. 9 wherein the image of a mask 52 which may be similar to one or another of masters 20 and 30 (FIGS. 3 and 4) is projected upon the lens, e.g. lens 12 to be coded. A suitable projection system may include a light collimating lens 54 and objective lens 56 wherewith ultraviolet radiation 58 from a suitable source 60 may be projected upon lens 10 in the form of image of the coding characters formed upon mask 52. Lenses 54 and 56 are formed of a material which is readily transmissive to the relatively short wavelengths of ultraviolet radiation, e.g. quartz.

Those skilled in the art will readily appreciate that there are various modifications nd adaptations of the precise forms of the invention here shown which may suit particular requirements and that the foregoing illustrations are not to be interpreted as restrictive of the invention beyond that necessitated by the following claims.

We claim:

1. The method for marking lenses comprising the steps of:
   preparing a mask of coding characters for disposition over one surface of a lens to be marked, said mask comprising opaques forming the configurations of said coding characters;
   disposing said mask intermediately of said lens and a source of particular wavelengths of radiant energy preselected for effecting a refractive index change in the material of said lens by exposure;
   exposing portions of said lens around said opaques of said mask to said radiant energy for a period of time sufficient to alter the refractive index of said lens material in said portions around said opaques substantially without affect upon remaining portions protected by said opaques whereby the resulting differential of refractive index in said lens produces a detectable facsimilie of said coding characters.

2. The method according to claim 1 wherein said opaques form the boundaries of said configurations of said coding characters and said exposed portions of said lens altered in refractive index by said exposure to said radiant energy are in the shape of said coding characters.

3. The method according to claim 1 wherein said opaques are in the configurations of said coding characters themselves and said exposed portions of said lens include the surrounds of the configurations of said coding characters, said surrounds being altered in refractive index by said exposure to said radiant energy.

4. The method according to claim 1 wherein said mask includes a slide of material which is highly transparent to said particular wavelengths of radiant energy and said opaques are applied to said slide.

5. The method according to claim 4 wherein said slide is formed of quartz.

6. The method according to claim 4 wherein said slide is placed adjacent to one surface of said lens.

7. The method according to claim 1 wherein said opaques are applied directly to one surface of said lens.

8. The method of claim 1 wherein said particular wavelengths of radiant energy are within the ultraviolet region of the electromagnetic spectrum.

9. The method according to claim 1 wherein said step of exposing portions of said lens is effected by optically projecting an image of said mask upon said lens.

10. The method according to claim 9 wherein the radiation used to project said image of said mask is within the ultraviolet region of the electromagnetic spectrum.

* * * * *